United States Patent [19]

Becht

[11] Patent Number: 4,565,199
[45] Date of Patent: Jan. 21, 1986

[54] LIGATOR

[75] Inventor: Carl T. Becht, Cincinnati, Ohio
[73] Assignee: Senmed, Inc., Cincinnati, Ohio
[21] Appl. No.: 142,675
[22] Filed: Apr. 22, 1980
[51] Int. Cl.⁴ .............................................. A61B 17/12
[52] U.S. Cl. ..................................... 128/325; 72/410; 29/243.56
[58] Field of Search ................... 128/325, 334 R, 326; 72/410; 29/243.56; 227/DIG. 1, DIG. 1 B, DIG. 1 C

[56] References Cited
U.S. PATENT DOCUMENTS

| | | | |
|---|---|---|---|
| 3,581,551 | 6/1971 | Wilkinson | 227/DIG. 1 B X |
| 3,732,719 | 5/1973 | Pallotta | 227/DIG. 1 B X |
| 3,775,826 | 12/1973 | Reed | 227/DIG. 1 B X |
| 3,780,416 | 12/1973 | Rider | 29/212 D |
| 4,226,242 | 10/1980 | Jarvik | 128/325 |

Primary Examiner—Michael H. Thaler
Attorney, Agent, or Firm—Frost & Jacobs

[57] ABSTRACT

A surgical ligator to locate and clamp a substantially U-shaped clip about a tubular member such as a blood vessel or the like, to close off the tubular member. The ligator comprises first and second handle elements pivoted in pliers-like fashion and terminating at their forward ends in clamping jaw portions. The first handle element has a longitudinal cavity formed therein comprising a magazine for a row of clips arranged in edge-to-edge relationship. The jaw portions of the first and second handle elements each have a locator stop for the forwardmost clip of the row to properly position the forwardmost clip for use. The longitudinal magazine of the first handle element has a spring actuated shoe therein to constantly urge and advance the row of clips forwardly to position the forwardmost clip of the row against the locator stops. The first and second handle elements and their jaw portions are pivotable between a normal open position and a closed clip-clamping position. A spring is provided to bias the handle elements and their jaw portions to the normal open position.

8 Claims, 16 Drawing Figures

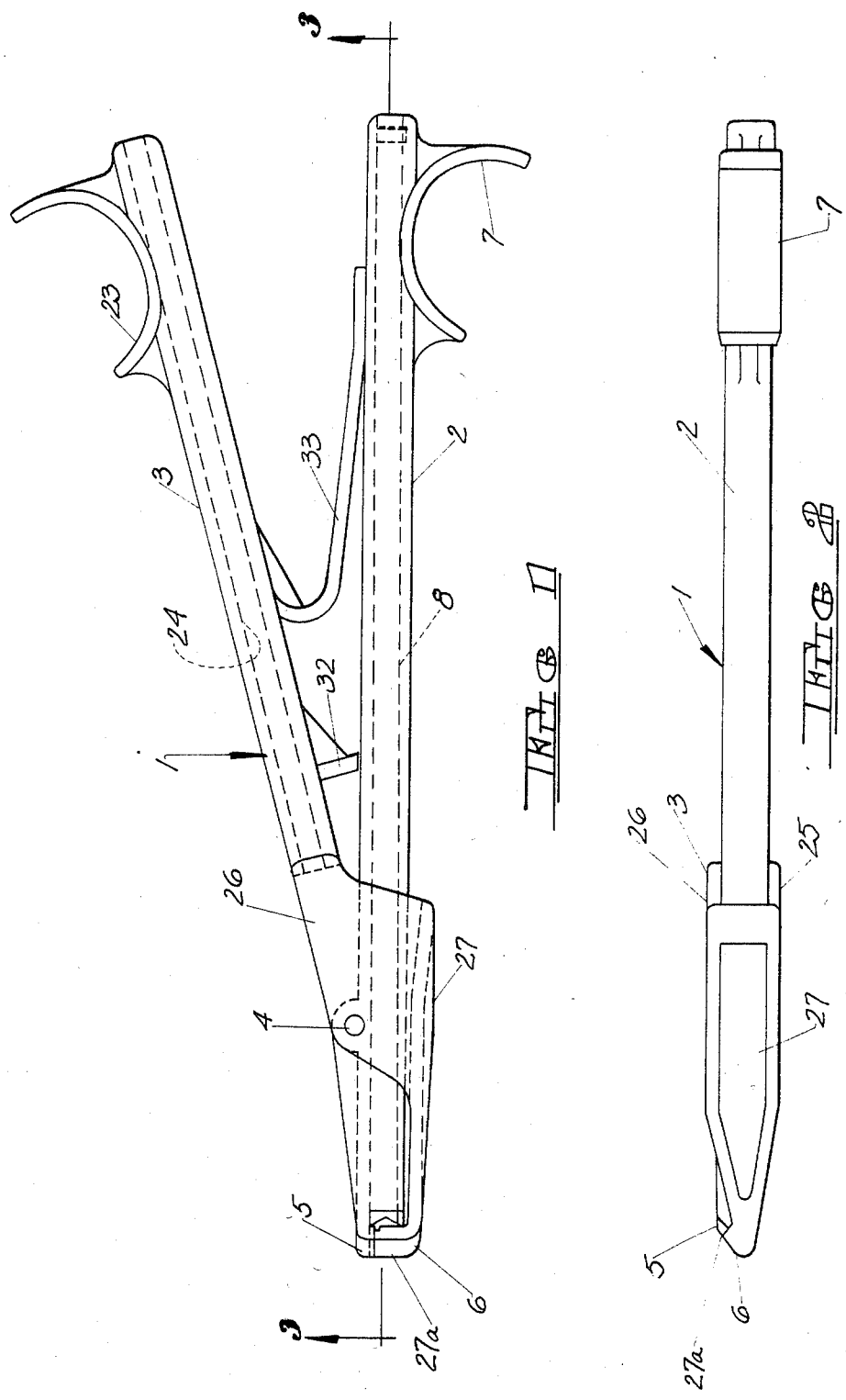

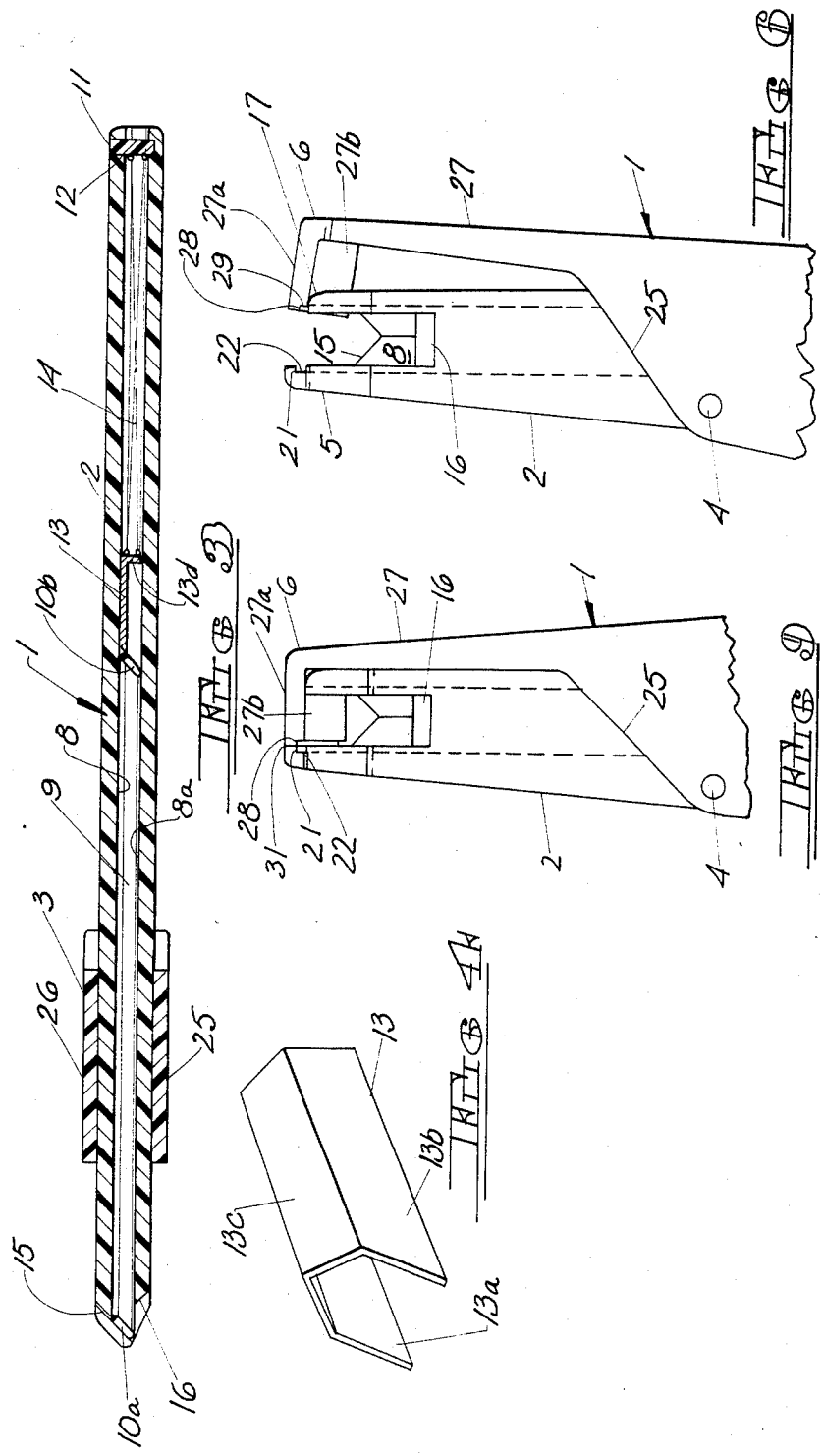

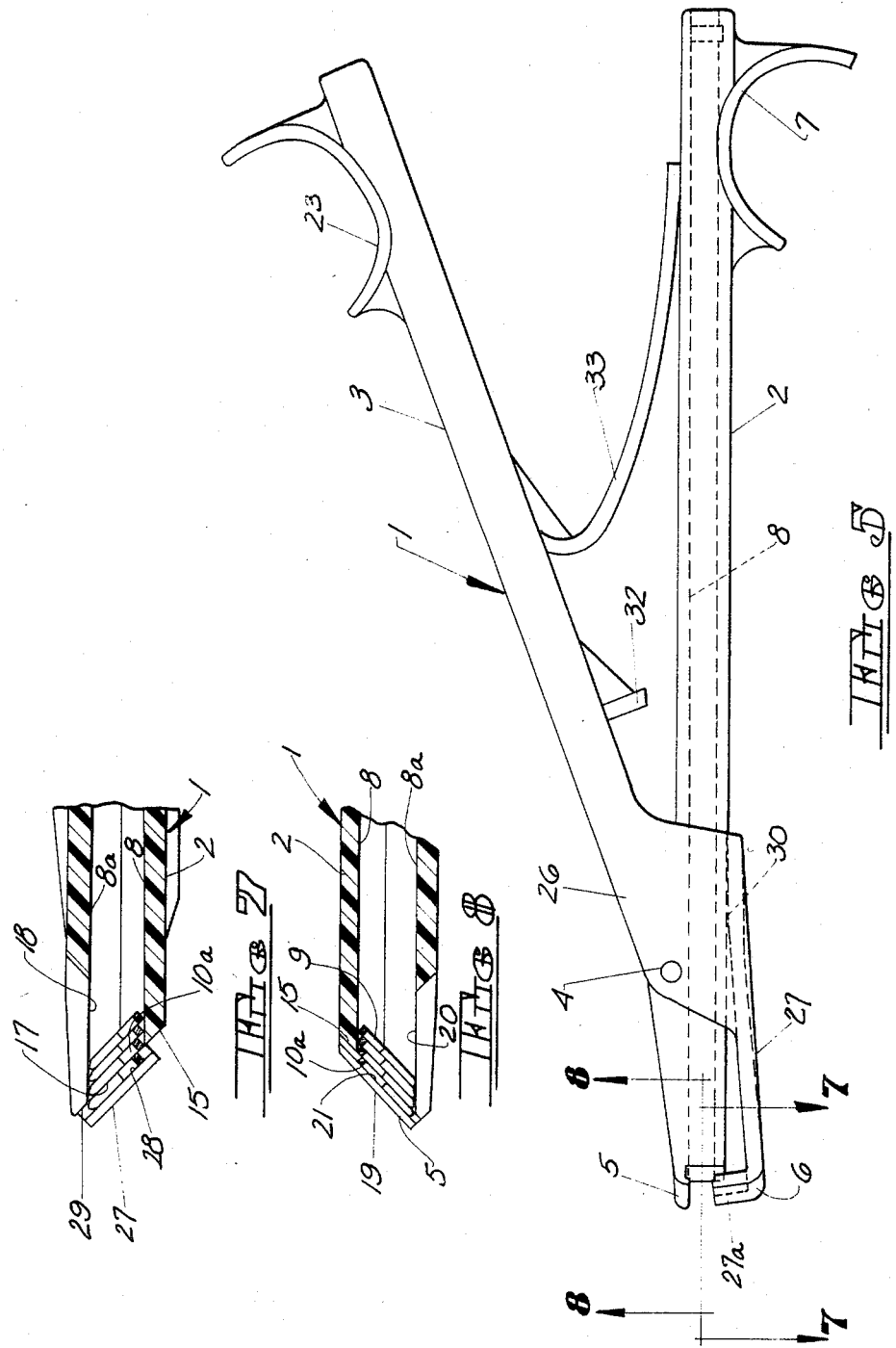

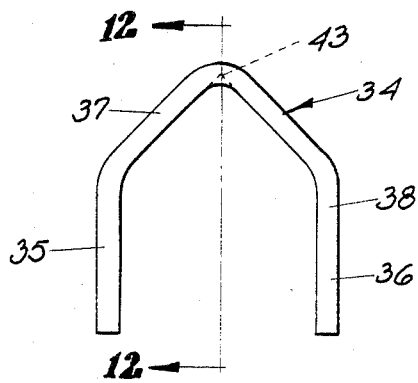
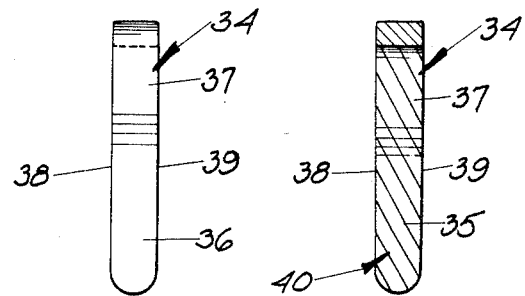
FIG. 10  FIG. 11  FIG. 12
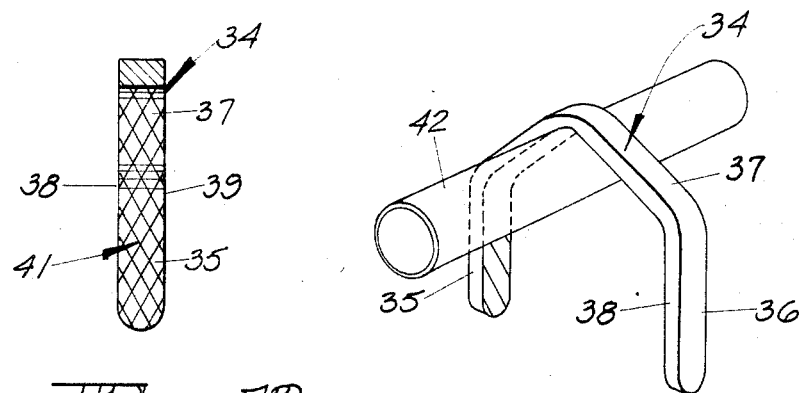
FIG. 13
FIG. 14
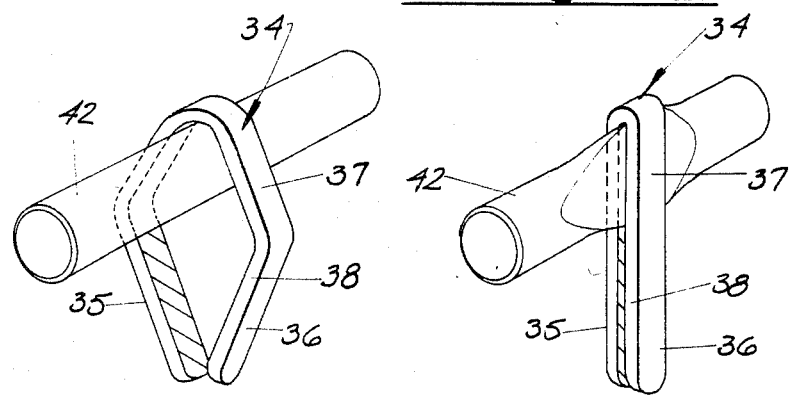
FIG. 15  FIG. 16

LIGATOR

TECHNICAL FIELD

The invention relates to a surgical ligator, and more particularly to such a ligator having a magazine for a row of clips located in one of its handle elements with means constantly urging the forwardmost clip of the row into position for use.

BACKGROUND ART

Prior art workers have devised many types of ligators, including ligators which apply a knotted loop of gut or synthetic suture material to the tubular member. Such ligators are taught, for example, in U.S. Pat. Nos. 3,687,138; 4,038,988 and 4,050,465.

A great many of the prior art ligators, however, are intended to apply a generally U-shaped clip to clamp the tubular member. U.S. Pat. Nos. 3,777,538; 3,867,944 and 4,027,370 are examples of such surgical devices wherein each clip is individually located in the jaws of the instrument, no magazine or cartridge being used. U.S. Pat. Nos. 3,631,707; 3,774,438 and 3,827,277 are exemplary of those surgical clip applicators utilizing a separate magazine or cartridge. In this instance, the surgical instrument is used to engage and withdraw a clip from the separate magazine, and thereafter to apply the clip to the tubular member.

Prior art workers have also developed surgical ligators having cartridges either built into the instrument or affixed thereto as an attachment. In most instances, the clips are located in the cartridge in end-to-end relationship, one behind the other, feeding legs foremost. This arrangement greatly reduces the number of clips which can be contained in the cartridge. Examples of such instruments are taught in U.S. Pat. Nos. 2,968,041; 3,006,344; 3,082,426; 3,740,994 and 3,844,289. U.S. Pat. No. 3,581,551 teaches a surgical clamp applying instrument having a vertical stack of clamps. In U.S. Pat. Nos. 3,576,288 and 3,592,377 the clips are mounted on and advanced by a threaded member. Finally, U.S. Pat. No. 2,874,384 describes a ligator having a small magazine of clips in face-to-face relationship and extending laterally of the instrument.

The prior art ligators provided with magazines or cartridges of clips are characterized by a number of disadvantages. First of all, the cartridges or magazines are of limited capacity and, in most instances, the orientation of the clips within the magazine or cartridge contribute to this limited capacity. In many instances, a part of the force utilized to actuate the prior art ligators is required to shift a clip to its position wherein it may be applied to the tubular member intended to be clamped. In some instances, wholly separate manipulation of the cartridge or magazine device is required.

The present invention constitutes an improvement over prior art ligators. The ligator herein described is a pliers-like structure having a pair of handle elements terminating at their forward ends in jaw portions. The first handle element contains a magazine for a row of clips arranged in edge-to-edge relationship. The jaw portion of the first handle element has a stop means to properly locate the forwardmost clip of the row in position for use. The jaw portion of the second handle element also has a locator stop. Means are provided within the magazine to constantly urge and advance the row of clips forwardly so that the forwardmost clip of the row will always be in position for use. Thus, no portion of the force required to operate the ligator is used to advance the clips.

The size of the magazine and the orientation of the clips therein enable the provision of a large number of clips within the magazine. The arrangement of the jaw portions is such that the jaws provide front and side containment of the forwardmost clip of the row thereof, while the next succeeding clip in the row (or ultimately the shoe) provides rearward containment for the forwardmost clip. The ligator of the present invention is extremely simple in design and construction and may be provided in both reusable and disposable forms.

DISCLOSURE OF THE INVENTION

In accordance with the invention there is provided a surgical ligator to locate and clamp a substantially U-shaped clip about a tubular member such as a blood vessel or the like to close off the tubular member. The ligator comprises a pair of handle elements pivotally joined together in pliers-like fashion. The handle elements terminate at their forward ends in clamping jaw portions.

A first one of the handle elements has a longitudinal cavity formed therein and extending from its rearward end to its forward jaw portion. This longitudinal cavity comprises a magazine to receive a row of clips arranged in edge-to-edge relationship. The jaw portion of this handle element also has a locater stop to properly locator and maintain the forwardmost clip of the row in position for application to a tubular member. The longitudinal magazine of the first handle element has a spring actuated shoe therein which constantly urges and advances the row of clips forwardly so that the first clip of the row is properly located in position for use.

The handle elements and their forwardmost jaw portions are pivotable between a normal open position and a closed clip-clamping position. Spring means are provided in association with the handle elements to bias the handle elements to their open position. The jaw portion of the second handle element also has a locator stop for the forwardmost clip of the row, when the jaw portions are in their open position. As the jaw portions pivot to their closed, clip-clamping position, the jaw portion of the second handle element shifts across the front of the magazine and flattens the forwardmost clip against the jaw portion of the first handle element.

The ligator of the present invention may be made in a reusable form of metal or other appropriate material suitable for use in a surgical environment and capable of withstanding sterilization by one or more of the well known methods. The simplicity of the structure is such that the ligator also lends itself well to being molded of an appropriate plastic material so that it can be provided in the form of a single-use, disposable instrument.

BRIEF DESCRIPTION OF THE DRAWINGS

FIG. 1 is a top plan view of the ligator of the present invention.

FIG. 2 is a side elevational view of the ligator of FIG. 1.

FIG. 3 is a cross sectional view taken along section line 3—3 of FIG. 1.

FIG. 4 is a perspective view of an exemplary form of shoe for use with the ligator of the present invention.

FIG. 5 is a top plan view of the ligator, similar to FIG. 1, but illustrating the handle elements and their jaw portions in their normal open position.

FIG. 6 is a fragmentary bottom view of the jaw portions of the ligator in their normal open position.

FIG. 7 is a fragmentary cross sectional view taken along section line 7—7 of FIG. 5.

FIG. 8 is a fragmentary cross sectional view taken along section line 8—8 of FIG. 5.

FIG. 9 is a fragmentary bottom view of the jaw portions of the ligator, similar to FIG. 6, but illustrating the jaw portions in their closed, clip-clamping position.

FIG. 10 is a front elevational view of a clip for use with the ligator of the present invention.

FIG. 11 is side elevational view of the clip of FIG. 10, as viewed from the right in that Figure.

FIG. 12 is a cross sectional view taken along section line 12—12 of FIG. 10.

FIG. 13 is a cross sectional view, similar to FIG. 12, illustrating a different knurl pattern on the inside surface of the clip.

FIG. 14 is a fragmentary perspective view of the clip of FIG. 10 as initially located about a tubular member to be clamped.

FIG. 15 is a fragmentary perspective view, similar to FIG. 14, and illustrating the clip in an intermediate stage of the clamping process.

FIG. 16 is a fragmentary perspective view, similar to FIGS. 14 and 15, and illustrating the clip in its fully clamped position about the tubular member.

BEST MODE OF CARRYING OUT THE INVENTION

Reference is first made to FIGS. 1 and 2 wherein like parts have been given like index numerals. The ligator is generally indicated at 1 and comprises a first handle element 2 and a second handle element 3 pivotally joined together by pivot pin 4. The first handle element 2 terminates at its forward end in a jaw portion 5. Similarly, the second handle element 3 has a jaw portion 6 at its forward end.

As indicated above, the ligator 1 of the present invention could be manufactured of stainless steel or other appropriate material for use in a surgical environment so as to constitute a permanent, reusable, sterilizable surgical appliance. The simplicity of its structure, however, lends itself well to be molded of plastic material such as glass filled polycarbonate, glass filled nylon, or the like, so as to constitute a single-use, disposable surgical appliance. For purposes of an exemplary showing, the ligator 1 is illustrated herein as being molded of such a plastic material.

Reference is now made to FIGS. 1 through 3. The first handle element 2 is of substantially rectangular cross section and may be provided at its rearward end with an arcuate finger grip element 7. Throughout its length, the first handle element 2 has a longitudinal cavity 8 formed therein. The cavity 8 comprises a magazine for the receipt of a row 9 of clips. In FIG. 3, the row 9 of clips is illustrated semi-diagrammatically, in edge-to-edge relationship the forwardmost and rearwardmost clips being fully illustrated at 10a and 10b, respectively.

When a clip is applied to a tubular member such as a blood vessel or the like, the clip will be oriented at about 90° to the tubular member. The ligator 1 of the present application will be oriented at approximately 45° to the tubular member during the clip-applying step. As a result of this, the clips of row 9 will slope rearwardly in magazine 8, lying at an angle of approximately 45° to the bottom surface 8a of magazine 8, as shown in FIG. 3. The cross sectional configuration of magazine 8 will depend upon the shape of the clips of row 9 and should be such as to just nicely receive the row 9 of clips in such a way that the row 9 of clips is readily advanceable through the magazine with the individual clips of the row maintaining their proper alignment.

Since the cavity constituting magazine 8 extends through the length of the first handle element 2, the clips may be inserted in the magazine from the rearward end of handle 2. The rearward end of handle 2 may thereafter be closed by any appropriate means. For purposes of an exemplary showing, a plug 11 is illustrated as being inserted in a slot 12 extending partway through first handle element 2 and transversely thereof.

Located immediately behind the row 9 of clips there is a shoe 13. The shoe is most clearly shown in FIGS. 3 and 4 and comprises an elongated member which may have substantially the same configuration as the clips mounted within magazine 8. This is shown by a comparison of FIGS. 4 and 10. FIG. 10 illustrates an exemplary clip which will be described hereinafter. The shoe of FIG. 4 is shown as comprising a pair of downwardly depending sides 13a and 13b joined together by an inverted V-shaped upper portion 13c. The shoe 13 is closed at its rear end, as at 13d (see FIG. 3), and is open at its forward end, the forward edges sloping rearwardly at an angle of about 45°, to match the slope of the rearwardmost clip 10b of row 9.

Immediately behind shoe 13, a compression spring (semi-diagrammatically illustrated in FIG. 3 at 14) is located in magazine 8. The forward end of compression spring 14 abuts the rear end 13d of shoe 13 while the rear end of spring 14 abuts plug 11. The spring 14 and shoe 13 cooperate to constantly urge and advance the row 9 of clips to locate the forwardmost clip 10a of the row in position for use. Thus, the advancement of the clips of row 9 is essentially automatic and wholly separate from the force required to actuate the ligator 1.

Referring to FIG. 3, at the forward end of first handle 2 the upper surface of the handle terminates in an upwardly and rearwardly sloping edge 15, sloping at an angle of about 45°. The bottom surface of first handle 2 terminates in an edge 16 which slopes rearwardly and downwardly at an angle of about 45°.

FIG. 5 is a plan view of the ligator 1 and FIG. 7 is a cross sectional view taken along section line 7—7 of FIG. 5. It will be noted from these Figures that the upper side of first handle element 2 (as viewed in FIG. 5) terminates in a downwardly and forwardly sloping front edge 15, again at an angle of about 45° to the bottom surface 8a (FIG. 7) of magazine 9. The bottom surface 8a continues along the lower side wall (as viewed in FIG. 5) in the form of a rail 18 along which one leg of each of the clips of the row 9 can slide. This is clearly shown in FIG. 7.

The upper side of first handle element 2 (as viewed in FIG. 5) terminates in a forward edge 19 which slopes forwardly and downwardly, again at an angle of about 45° to the bottom surface 8a of magazine 8. This is shown in FIG. 8. Once again, the bottom surface 8a of magazine 8 continues nearly to this forward edge in the form of a rail 20 along which the other legs of the clips can slide.

The forward edge 19 of the upper side of first handle element 2 (as seen in FIG. 5) extends further forward than the forward edge 17 of the lower side and is hook-shaped, as is most clearly seen in FIG. 6. This forms a forward surface 21 which slightly overlaps the forward end of magazine 8 and constitutes a locator stop for the forwardmost clip 10a of row 9. The locator stop or surface 21 again lies at an angle of about 45° to the bottom surface of the magazine 8. The edge 15 of the top portion of first handle element 2 is spaced from the surface 21 by a distance slightly greater than the thickness of a clip, as is rail 20. This produces a surface 22 (FIG. 6) between the locator stop 21 and edge 15 and the forward end of rail 20 which constitutes a clamping surface used to close a clip and serving to make the forward end of the upper side of first handle element 2 (as seen in FIG. 5) constitute the clamping jaw 5. (See also FIG. 6).

Reference is now made to FIGS. 1, 2, 3 and 6 for a description of the second handle element 3. The second handle element 3 may be provided at its rearward end with an arcuate finger grip 23 similar to arcuate finger grip 7. Since the embodiment illustrated is molded of a plastic material, the straight longitudinal rearward portion of second handle element 3 may have an axial bore 24 formed therein for purposes of material savings. At the forward end of that portion of the second handle element 3 containing axial bore 24, the handle element is bifurcated. Bifurcations 25 and 26 are illustrated in FIGS. 3 and 6. The first handle element 2 passes between birfurcations 25 and 26, as described above, and is pivotally attached to the bifurcations 25 and 26 by pivot pin 4.

The bifurcations 25 and 26 are joined by a side wall 27 which, at its forward end, is generally hook-shaped, having a portion 27a extending substantially at right angles thereto and sloping upwardly and rearwardly at an angle of about 45°. The inside corner of the free end of portion 27a is notched to form a first upwardly and rearwardly sloping surface 28 similar to surface 21 of first handle element 2 and also serving as a locator stop for the forwardmost clip 10a of row 9. The notch also forms a second surface 29 extending upwardly at an angle of about 45° and constituting a clamping surface similar to clamping surface 22 and adapted to cooperate therewith to close the forwardmost clamp 10a of row 9 about a tubular member. Thus, the forward end of second handle element 3 constitutes a jaw, heretofore designated 6. The portion 27a of wall 27 of second handle element 3 has an inside surface 27b (see FIGS. 6 and 9) which slopes upwardly and rearwardly at an angle of about 45° and just clears the forward edge 17 of the right side of first handle element 2 (as viewed in FIG. 6).

The first and second handle elements 2 and 3, joined together by pivot pin 4, are swingable between a normal open position and a closed clip-clamping position. FIGS. 5 and 6 illustrate the ligator with its first and second handle elements 2 and 3 and its jaws 5 and 6 in their normal open position. This normal open position is determined by the abutment of the inside surface of wall 27 of second handle element 3 against the side of first handle element 2, as at 30 in FIG. 5. The closed clip-clamping position of jaws 5 and 6 and first and second handle elements 2 and 3 is determined first of all by abutment of the jaws as at 31 in FIG. 9. It is also determined by abutment of a stop means 32, formed on second handle element 3 against the side of first handle element 2. This relieves the forces on pivot pin 4.

To complete the structure, a spring means is provided to bias the first and second handle elements 2 and 3 and jaws 5 and 6 to their normal open position. For purposes of an exemplary showing, the ligator 1 is shown in FIGS. 1 and 5 as being provided with a leaf spring 33 constituting an integral one-piece part of second handle element 3. The free end of leaf spring 33 abuts the first handle element 2 and tends to urge the first and second handle elements 2 and 3 and the jaws 5 and 6 to their normal open position as shown in FIG. 5. It will be understood by one skilled in the art that a metallic leaf spring or other spring-like device could be substituted for the molded plastic spring 33, if desired.

An exemplary and preferred embodiment of ligator clip is generally indicated at 34 in FIGS. 10 through 12. The clip 34 may be made of any appropriate material suitable for use in a surgical environment and for permanent residence in the human body. Tantalum, for example, has been found to be excellent for this purpose.

The clip 34 is generally of inverted U-shaped configuration having parallel leg portions 35 and 36 and a bridge or crown portion 37. While the crown portion may be arcuate, it is preferred that it have an inverted V-shaped configuration as shown in FIG. 10.

The clip has edges 38 and 39 (see FIG. 11) and when a plurality of clips are arranged in a row, the edges 39 of one clip is in abutment with the edges 38 of the next adjacent clip, and so on, as shown in FIGS. 3, 7 and 8. This, therefore, is what is meant by the phrase "edge-to-edge relationship" as used herein and in the claims.

To aid in gripping the tubular member to be clamped off, it is preferred that the inside surface of the legs 35 and 36 and the crown portion 37 be knurled. In FIG. 12, the inside surface of leg 35 and the adjacent portion of crown 37 are shown as being provided with diagonal knurling generally indicated at 40. Preferably, the remainder of crown 34 and leg 36 will be similarly knurled but in the opposite direction. Alternatively, the inside surfaces of legs 35 and 36 and crown portion 37 can be double knurled as is generally indicated at 41 in FIG. 13.

FIGS. 14 through 16 illustrate the application of clip 34 to a tubular member 42 such as a blood vessel. The ligator 1 (not shown) is caused to approach the tubular member 42 at an angle of about 45° thereto and the tubular member 42 is received between ligator jaws 5 and 6. The forwardmost clip of the row thereof is therefore located over tubular member 42 and at right angles thereto, as shown in FIG. 14. As the jaws of the ligator approach each other, the uppermost portion of the crown will bend first bringing the free ends of the clip legs 35 and 36 together as shown in FIG. 15. When the jaws 5 and 6 of ligator 1 are pivoted to their fully closed, clip-clamping position, the leg and crown portions of the clip are closed against each other with the tubular member 42 firmly clamped therebetween as shown in FIG. 16. To assure that the crown portion of the clip first bends during the clip-applying procedure (in the manner shown in FIG. 15), it is within the scope of the invention to provide a notch (shown in broken lines at 43 in FIG. 10) on the inside surface of the crown portion of the clip at the position where the bend is to take place.

The ligator 1 and the clip 34 having been described in detail, the mode of operation of the ligator may be set forth as follows. The ligator is grasped by the surgeon with his thumb engaged in finger grip 7 and his middle finger (for example) engaged in finger grip 23. The ligator will normally be in its open position as illustrated in FIG. 5. The cooperation of shoe 13 and compression spring 14 will assure that the forwardmost clip 10a of row 9 will be in abutment with locater stop 21 of jaw 5 and locator stop 28 of jaw 6. The ligator 1 is caused to approach the tubular member to be closed at an angle of about 45° thereto, with the tubular member located between jaws 5 and 6. Thereafter, the surgeon squeezes first and second handle element 2 and 3 toward each other and against the action of leaf spring 33. The jaw surface 22 of jaw 5 and the jaw surface 29 of jaw 6 will engage the legs of the forwardmost clip. Continued actuation by the surgeon will cause jaw 6 to wipe across the magazine 8 placing and clamping the forwardmost clip of row 9 in the manner described with respect to FIG. 14 through 16. The ligator jaws are then permitted to pivot toward their open position by the surgeon and the ligator is lifted away from the tubular member having been clamped, thereby removing the clamped clip from the ligator. The shoe 13 and compression spring 14 will immediately assure that the next adjacent clamp, now the forwardmost clamp of row 9, will abut locator stop surface 21 of jaw 5. If jaw 6 is not yet fully opened, the clip will simply abut the inside surface 27b of jaw 6. When jaw 6 reaches its fully open position, the clip will abut its locator stop surface 28 and the ligating procedure can be repeated.

Modifications may be made in the invention without departing from the spirit of it.

What is claimed is:

1. A surgical ligator to locate and clamp a substantially inverted U-shaped clip about a tubular body member to close off the tubular member, said ligator comprising first and second handle elements pivoted together in pliers-like fashion and terminating at their forward ends in clamping jaw portions, said first and second handle elements and their clamping jaw portions being pivotable between a normal open position and a closed clip-clamping position, means in association with said handle elements to bias said handle elements and their clamping jaw portions to said normal open position, said first handle elements having a longitudinal cavity formed therein comprising a magazine for a row of clips arranged in edge-to-edge relationship, said row of clips being located within said magazine and extending longitudinally of said first handle element, said clamping jaw portion of at least one of said handle elements having a locator stop for the forwardmost clip of said row to properly position said forwardmost clip for use, and means in said magazine independent of tool actuation energy to constantly urge and advance said row of clips to position said forwardmost clip of said row against said locator stop.

2. The structure claimed in claim 1 including a second locator stop on said clamping jaw portion on the other of said handle elements, said second locator stop being contacted by said forwardmost clip of said row when said first second handle elements and their clamping jaw portions are in said normal open position.

3. The structure claimed in claim 1 including a shoe slidably mounted in said magazine and being in abutment with the rearwardmost clip of said row, and a compression spring in said magazine, behind said shoe, to constantly urge and advance said shoe and thus said row of clips to position said forwardmost clip of said row against said locator stop.

4. The structure claimed in claim 1, including a second locator stop on said clamping jaw portion on the other of said handle elements, said second locator stop being contacted by said forwardmost clip of said row when said first and second handle elements and their clamping jaw portions are in said normal open positions and including a shoe slidably mounted in said magazine and being in abutment with the rearwardmost clip of said row, and a compression spring in said magazine, behind said shoe, to constantly urge and advance said shoe and thus said row of clips to position said forwardmost clip of said row against said locator stop, said row of clips being contained at their front and sides by said jaws, and longitudinally between said locator stops and said shoe.

5. The structure claimed in claim 1 wherein said means to bias said handle elements and their clamping jaw portions to said normal open position comprises a leaf spring, one end of said leaf spring being affixed to one of said first and second handle elements, the other end of said leaf spring being free and constantly abutting the other of said first and second handle elements.

6. The structure claimed in claim 1 wherein said handle elements and their clamping jaw portions of said ligator are molded of a plastic material suitable for use in a surgical environment.

7. The structure claimed in claim 1, wherein said jaws are provided with rails constituting extensions of said magazine.

8. A surgical ligator to locate and clamp a substantially inverted U-shaped clip about a tubular body member to close off the tubular body member, said ligator comprising first and second handle elements pivoted together in pliers-like fashion and terminating at their forward ends in clamping jaw portions, said first and second handle elements and their clamping jaw portions being pivotable between a normal open position and a closed clip-clamping position, means in association with said handle elements to bias said handle elements and their clamping jaw portions to said normal open position, said first handle element having a longitudinal cavity formed therein comprising a magazine for a row of clips arranged in edge-to-edge relationship, said row of clips being located within said magazine and extending longitudinally of said first handle element, said clips of said row leaning rearwardly in said magazine so as to lie at an angle of about 45° to the long axis of said magazine, said clamping jaw portion of at least one of said handle elements having a locator stop for the forwardmost clip of said row to properly position said forwardmost clip for use, and means in said magazine independent of tool actuation energy to constantly urge and advance said row of clips to position said forwardmost clip of said row against said locator stop.

* * * * *